United States Patent [19]

Sportelli et al.

[11] 4,266,139
[45] May 5, 1981

[54] COMPOSITE SHIELDING MEANS AND MOUNTING MEANS FOR X-RAY MACHINES

[76] Inventors: Louis Sportelli, 175 Delaware Ave., Palmerton, Pa. 18071; James F. Winterstein, 1443 Southridge Dr., Clearwater, Fla. 33516

[21] Appl. No.: 110,040

[22] Filed: Jan. 7, 1980

[51] Int. Cl.³ .................... G21F 1/00; G21C 11/00
[52] U.S. Cl. ................................ 250/515; 250/510
[58] Field of Search ............ 250/515, 519, 456, 451, 250/452, 510

[56] References Cited

U.S. PATENT DOCUMENTS

| | | |
|---|---|---|
| 2,426,884 | 9/1947 | Kieffer . |
| 3,233,248 | 2/1966 | Bushnell . |
| 3,631,249 | 12/1971 | Friede et al. . |
| 3,649,835 | 3/1972 | Brackenbrough .................. 250/515 |
| 3,678,233 | 7/1972 | Faw et al. . |
| 3,944,838 | 3/1976 | Gade . |
| 3,986,036 | 10/1976 | Harper et al. . |
| 4,082,957 | 4/1978 | Morlan . |
| 4,158,779 | 6/1979 | Rommel et al. ...................... 250/515 |
| 4,214,167 | 7/1980 | Gade ..................................... 250/515 |

Primary Examiner—Bruce C. Anderson
Attorney, Agent, or Firm—John S. Roberts, Jr.

[57] ABSTRACT

A shielding means for an x-ray machine comprised of a base plate which removably receives overlays masking out selective portions of the base plate to control the passage of the x-rays therethrough. The overlays are generally identical and provided with co-operating removable securing means to permit the same to be stacked one on the other to vary the thickness thereof. Removable mounting rails position and maintain the shielding means on the x-ray machine.

6 Claims, 10 Drawing Figures

U.S. Patent   May 5, 1981   Sheet 1 of 2   4,266,139
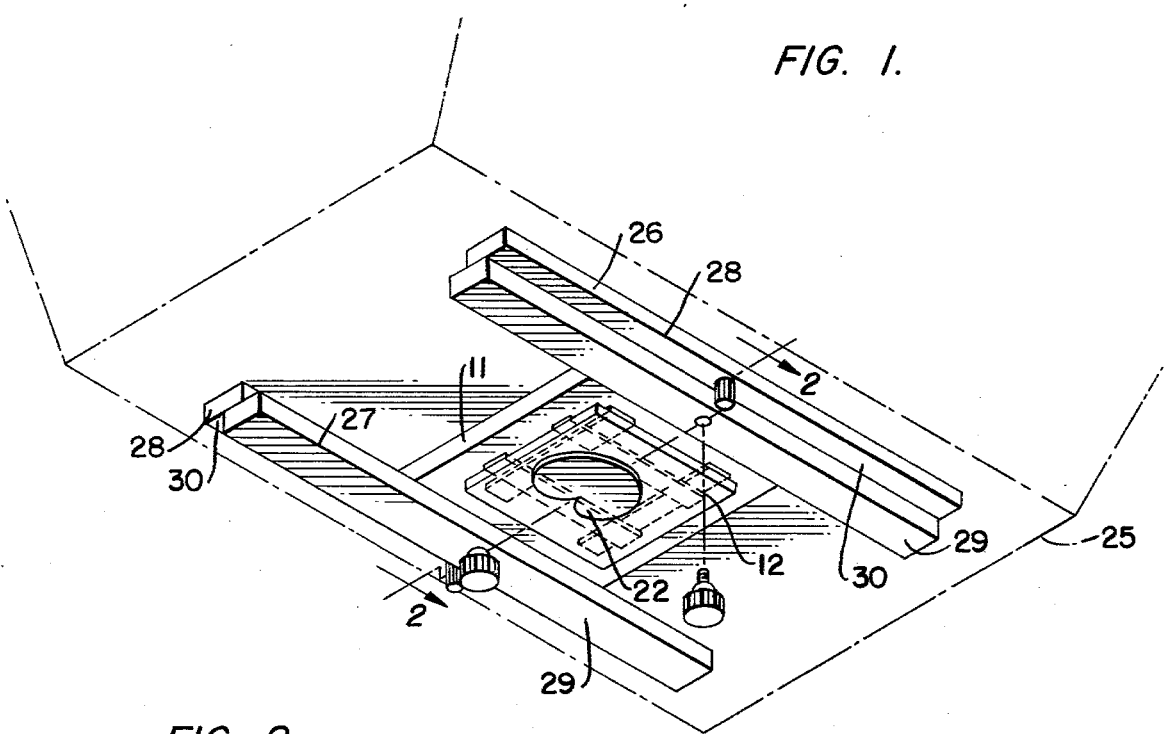
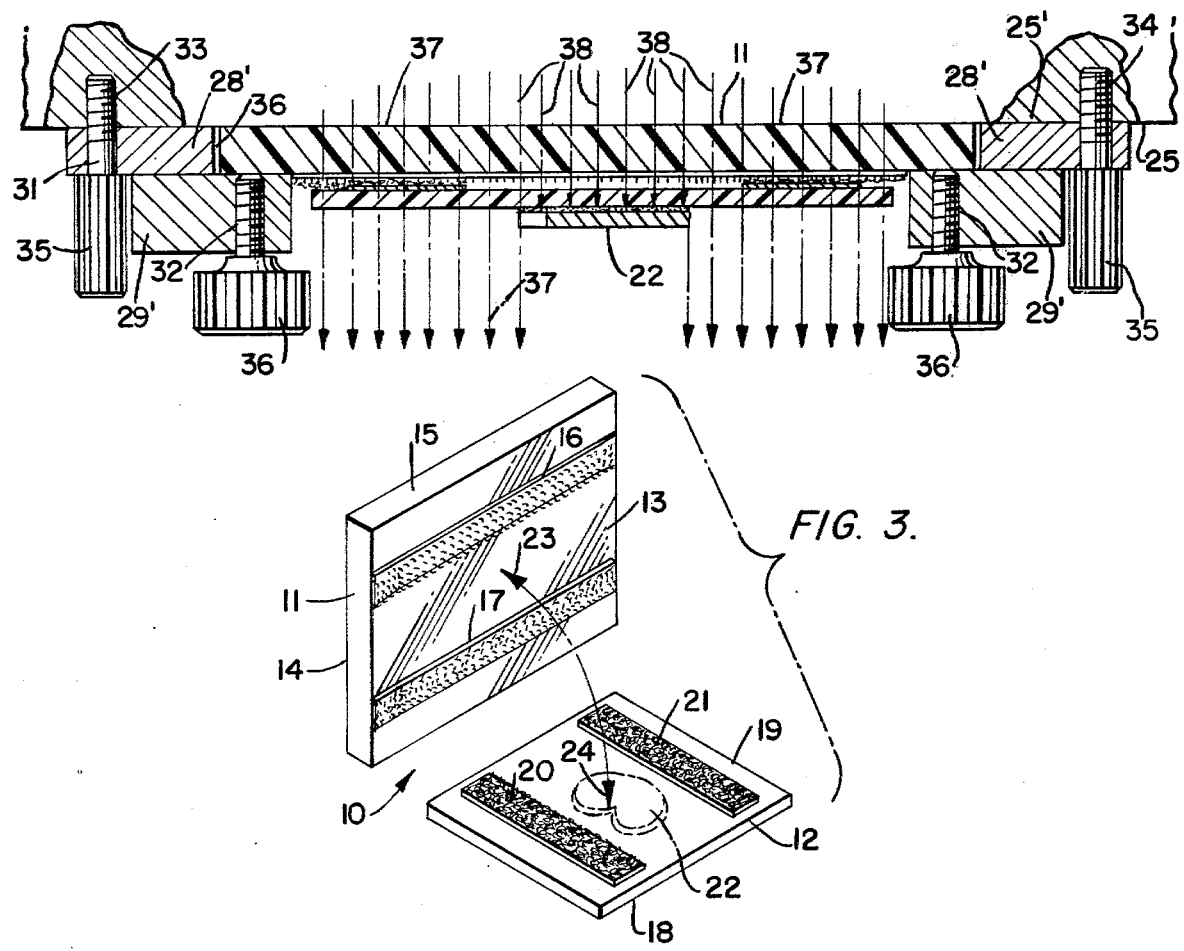

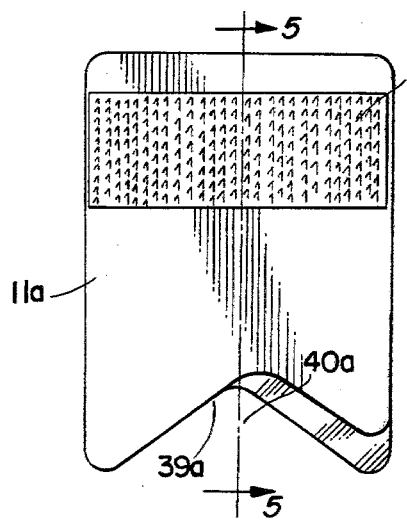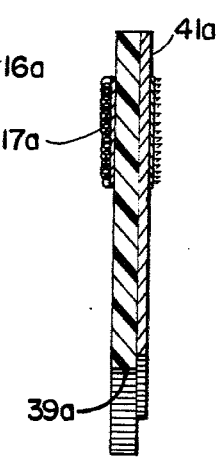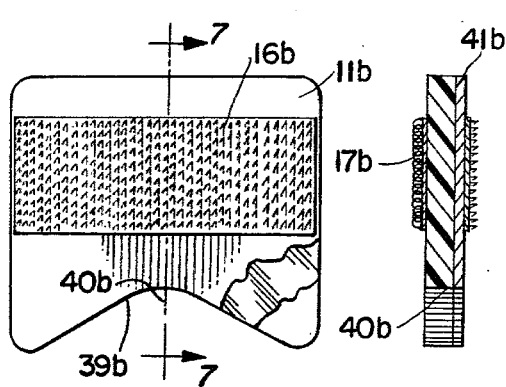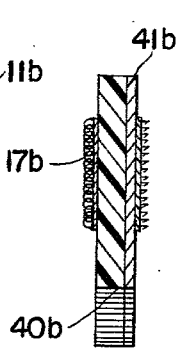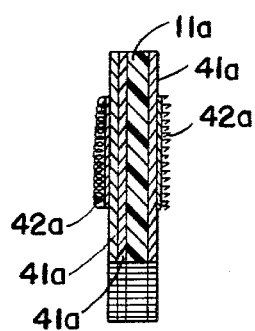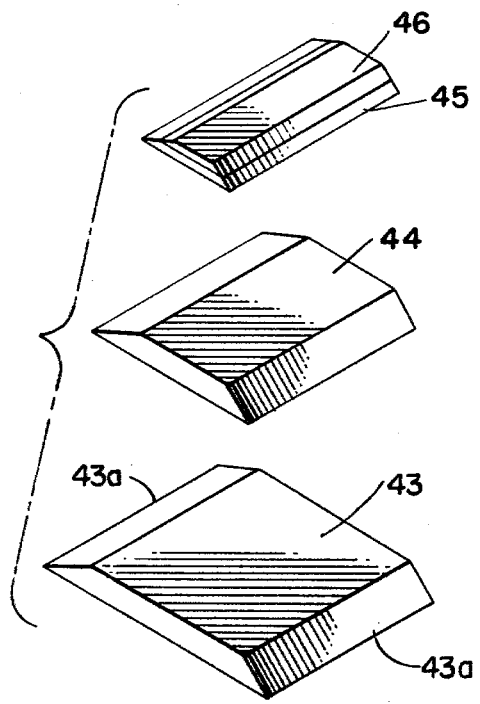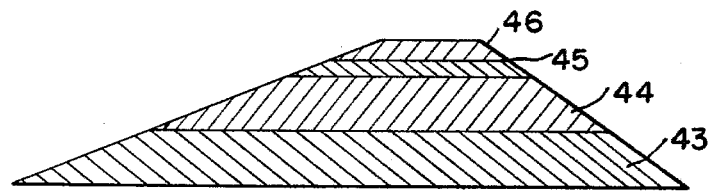

COMPOSITE SHIELDING MEANS AND MOUNTING MEANS FOR X-RAY MACHINES

BACKGROUND OF THE INVENTION

The prior art is aware of various devices adapted to be associated either with x-ray machines to shield various parts of a person's body or of an object or associated with the person or object which are to be treated by x-rays. These shields and their adaptability to either the x-ray machine or the person or object can be seen in U.S. Pat. Nos. 2,426,884; 3,233,248; 3,631,249; 3,678,233; 3,944,838; 3,986,036 and 4,082,957. These patents typify the general state of the art in this area.

SUMMARY OF THE INVENTION

The present invention relates to shielding devices for x-ray machines which can be readily assembled and mounted thereon in an economical, simple and efficient manner. Simply, the shielding device is comprised of a base member provided with a removable securing means adapted to receive and hold a masking overlay which also is provided with a mating removable means. In one embodiment the overlay can comprise a plurality of similar metallic sheets with co-operating fastening means whereby the thickness can be varied as desired. In another embodiment the overlay can be trapezoidal in shape to vary the passage of x-rays from the edges toward the body of the same.

Removable mounting rails of staggered profiles are utilized to mount and position the shields to the x-ray machine with the rails being reversible to accomodate base plates of varying thicknesses.

DESCRIPTION OF THE DRAWINGS

FIG. 1 is a perspective view showing the masking shield of the present invention mounted on an x-ray machine;

FIG. 2 is an end view of the masking shield of FIG. 1;

FIG. 3 is an exploded view showing the assembly of the masking shield of FIGS. 1 and 2;

FIGS 4-8 show a modification of other masking shields; and

FIGS. 9 and 10 show a further modification of another masking shield.

DESCRIPTION OF THE PREFERRED EMBODIMENT

The shield of the present invention is seen in FIG. 3 and is designated generally by the numeral 10 and is comprised of a base member 11 and a masking overlay 12. The base 11 is made from plastic and is of rectangular configuration having front and rear surfaces 13, 14 separated by a thickness 15 which can vary as desired. As seen a pair of spaced Velcro strips 16, 17 extending the length of the front surface 13 are adhesively secured thereto, and while Velcro is preferred, it is to be understood that any type of removably securing fastening means can be used with one of the prime considerations being that the same permits a bond between the base and the overlay 12.

The overlay 12 in this instance is also formed from clear plastic in rectangular fashion and defines a front and rear surface 18, 19. The rear surface 19 also has a pair of mating Velcro strips 20,21 adhesively secured thereto which straddles a lead shield 22 formed in gonadal shape, secured to the front surface 18. As is apparent the masking overlay 12 and its strips 20, 21 are removably secured to the base 11 and its strips 16, 17 by moving the same into and out of engagement therewith in the direction of the arrows 23, 24. When the overlay 12 is secured to the base 11 the shield 22 will prevent the passage of x-rays therethrough and thereby protect a specified area of the patient being treated. The shield 22 can take various shapes to protect other parts of a patients body.

The shield 10 is adapted to be placed and maintained in front of the x-ray discharge opening of a machine 25 shown in dotted outline in FIG. 1. The machine can be of any make, size or shape as mounting rails are provided along with the shields and are so designed to render their attachment to the machine notwithstanding its characteristics. Each of the rails 26, 27 are comprised of two rigid, elongated members 28, 29 staggered relative to one another as at 30 and are of a sufficient length to insure that the shield 10 can cover the x-ray discharge opening of the machine 25. It is to be noted that each of the elongated members 28, 29 are of different thicknesses, see FIG. 2 at 28', 29' for reasons to become apparent hereinafter. Openings 31, 31 are provided in each of the rails 28, 29 substantially medially thereof either of which can be aligned with openings 33, 34 in the machine 25 and maintained thereon by threadable fasteners 35, 35.

With the rails so mounted, see FIG. 2, the shield 10 is slid into the space 36 defined by the upper surface of the members 29, 29 and the bottom surface 25' of the machine 25 until it is disposed in front of the x-ray discharge opening. Threaded fasteners 36, 36 are then inserted into the openings 32, 32 to flushingly engage the front surface 13 of base 11 to frictionally lock the same in place. It is to be noted that the thickness of the base 11 approximates that of the rail 28 providing a tight compact relationship, however, if the base were of a thinner dimension it would only be necessary to use threaded fasteners 36, 36 of a longer length. Alternatively, if the base plate 11 were thicker, each of the rails 26, 27 could be inverted with the elongated members 29, 29 being utilized to mount the rails to the machine 25 to thereby provide a greater space 36 between the members 28, 28 and the bottom of the machine 25' to accomodate the greater thickness. In any event, with the shield in place as depicted in FIGS. 1 and 2 the plurality of rays 37, 37 emanating from the x-ray source are seen to pass through the transparent portions of the base and overlay to the person or object disposed in front of the machine. However, certain of the rays 38, 38 are seen to be stopped by the shield 22 and therefore that portion of the person or object will not be affected by the x-rays.

FIGS. 4 through 7 disclose other shapes of base plates 11a, 11b, respectively, functioning in the same general manner as that of the base 11 as previously described differing in that each of the plates are cut away at one end thereof in wedge shaped fashion, 39z, 39b, with the wedge 39a forming a defined apical portion 40a and the wedge 39b being curvilinear as at 40b. The base plates 11a, 11b are provided on both the front and rear surfaces 13a, 14a and 13b, 14b with Velcro strips 16a, 17a, and 16b, 17b whereby the same can co-operate with stainless steel plates of the same shape 41a, 41b provided with co-operating Velcro stips 42a', 43a on either side thereof. In this manner a plurality of the stainless steel plates can be stacked one on top of the other until a desired thickness is attained, exemplified in FIG. 8. This thickness is dependent on the thickness of the area to be x-rayed.

The shields of FIGS. 4-8 prevent the passage of x-rays therethrough except for the apical and curvilinear portions 39a and 39b, respectively to expect the localization of the same onto the patient or object positioned forwardly of the machine.

FIGS. 9 and 10 illustrate a further modification of a shield. Each of the shield elements 43, 44, 45 and 46 is fabricated from aluminum or stainless steel in trapezoidal shape which can be used individually or be stacked one on the other as shown in FIG. 10. Considering element 43 its tapered edges 43a permit a graduated resistance to the passage of the x-rays due to the increased thickness of the plate from the edges 43a, 43a toward the main body thereof. Consequently, the stacking of the elements can vary the thickness as desired of the overall shield. Velcro strips, not shown, are used in conjunction with the top and bottom surfaces of each of these elements to effect the stacking of these elements in the same manner as previously discussed.

Therefore, it is seen that by providing the mounting rails and the composite shields of the present invention a conventional x-ray machine of any make, size or shape can be simply modified to localize the passage of x-rays to any desired degree and to certain areas of a patient or object disposed in front of the same.

We claim:

1. A shielding device for an x-ray machine comprised of a transparent planar base member and a mounting means therefor: The planar base member consisting of a plurality of removable securing means mounted on one side thereof, a planar masking overlay with a cooperating securing means mounted on one side thereof adapted to removably engage the securing means of the base member, said overlay having a selected portion thereof being defined by x-ray impenetrable means whereby either a corresponding portion of a persons body or of an object will be protected by the selected portions; the mounting means therefor consisting of a pair of rails, each of which is comprised of an elongated member defining a staggered profile, openings disposed in the staggered profile, fastening means adapted to be inserted into each of the openings with one of the fasteners adapted to secure the elongated members to the x-ray machine, with the other fasteners frictionally engaging the base member to position the same on the x-ray machine.

2. The device of claim 1 wherein the thickness of the staggered profile of the elongated members vary with respect to one another to accomodate base plates of various thicknesses.

3. The device of claim 2 wherein the planar base member and the planar masking overlay are provided on both sides thereof with co-operating removable securing means whereby a plurality of overlays can be selectively and removably secured to either side of the base member and to one another to form a shield of varying thickness.

4. The device of claim 3 wherein the base plate and the overlays are of the same configuration.

5. The device of claim 3 wherein the overlays are of trapezoidal shape.

6. The device of claim 3 wherein the base member is made from plastic and the overlay from metal.

* * * * *